United States Patent
Lenormand

(10) Patent No.: US 9,206,456 B2
(45) Date of Patent: Dec. 8, 2015

(54) FORMATION OF PROTEOLIPOSOMES CONTAINING MEMBRANE PROTEINS BY MEANS OF AN ACELLULAR PROTEIN SYNTHESIS SYSTEM

(75) Inventor: Jean-Luc Lenormand, La Tronche (FR)

(73) Assignee: Universite Joseph Fourier, Grenoble (FR)

( * ) Notice: Subject to any disclaimer, the term of this patent is extended or adjusted under 35 U.S.C. 154(b) by 876 days.

(21) Appl. No.: 12/450,968

(22) PCT Filed: Apr. 25, 2008

(86) PCT No.: PCT/FR2008/050757
§ 371 (c)(1),
(2), (4) Date: Apr. 2, 2010

(87) PCT Pub. No.: WO2008/152262
PCT Pub. Date: Dec. 18, 2008

(65) Prior Publication Data
US 2010/0189774 A1   Jul. 29, 2010

(30) Foreign Application Priority Data
Apr. 26, 2007  (FR) ...................................... 07 54701

(51) Int. Cl.
*A61K 9/127* (2006.01)
*C12P 21/02* (2006.01)
*A61K 47/48* (2006.01)
*C07K 14/705* (2006.01)
*A61K 38/00* (2006.01)

(52) U.S. Cl.
CPC ............ *C12P 21/02* (2013.01); *A61K 47/48238* (2013.01); *A61K 47/48815* (2013.01); *C07K 14/705* (2013.01); *A61K 38/00* (2013.01)

(58) Field of Classification Search
USPC ........................................................ 424/450
See application file for complete search history.

(56) References Cited

U.S. PATENT DOCUMENTS

2007/0259420 A1* 11/2007 Greenbaum et al. .......... 435/325

OTHER PUBLICATIONS

Klammt et al. (FEBS Journal 273 (2006) 4141-4153).*
Berrier et al., Cell-free synthesis of a functional ion channel in the absence of a membrane and in the presence of detergent. Biochemistry. Oct. 5, 2004;43(39):12585-91.
Calhoun et al., Energizing cell-free protein synthesis with glucose metabolism. Biotechnol Bioeng. Jun. 5, 2005;90(5):606-13. Abstract only.
Douce et al., Isolation and properties of the envelope of spinach chloroplasts. J Biolog Chem. Oct. 25, 1973;248(10):7215-22.
Kim et al., Prolonging cell-free protein synthesis by selective reagent additions. Biotechnol Prog. May-Jun. 2000;16(3):385-90. Abstract only.
Kim et al., Rapid production of milligram quantities of proteins in a batch cell-free protein synthesis system. J Biotechnol. Jul. 13, 2006;124(2):373-80. Epub Feb. 17, 2006. Abstract only.
Klammt et al., Cell-free production of G protein-coupled receptors for functional and structural studies. J Struct Biol. Jun. 2007;158(3):482-93. Epub Jan. 23, 2007.
Klammt et al., Evaluation of detergents for the soluble expression of alpha-helical and beta-barrel-type integral membrane proteins by a preparative scale individual cell-free expression system. FEBS J. Dec. 2005;272(23):6024-38.
Lamla et al., The cell-free protein biosynthesis—applications and analysis of the system. Acta Biochim Pol. 2001;48(2):453-65. Review. Abstract only.
Liguori et al., Liposomes-mediated delivery of pro-apoptotic therapeutic membrane proteins. J Control Release. Mar. 20, 2008;126(3):217-27. Epub Dec. 14, 2007.
Liguori et al., Production of membrane proteins using cell-free expression systems. Expert Rev Proteomics. Feb. 2007;4(1):79-90. Review. Abstract only.
Marques et al., Liposome-mediated cellular delivery of active gp91(phox). PLoS One. Sep. 12, 2007;2(9):e856.
Rigaud, Membrane proteins: functional and structural studies using reconstituted proteoliposomes and 2-D crystals. Braz J Med Biol Res. Jul. 2002;35(7):753-66. Abstract only.
Spirin, High-throughput cell-free systems for synthesis of functionally active proteins. Trends Biotechnol. Oct. 2004;22(10):538-45. Review. Abstract only.
Swartz et al., Developing cell-free biology for industrial applications. J Ind Microbiol Biotechnol. Jul. 2006;33(7):476-85. Epub May 9, 2006. Review. Abstract only.
Templeton et al., Improved DNA: liposome complexes for increased systemic delivery and gene expression. Nat Biotechnol. Jul. 1997;15(7):647-52.

* cited by examiner

*Primary Examiner* — Janet Epps-Smith
(74) *Attorney, Agent, or Firm* — Wolf, Greenfield & Sacks, P.C.

(57) ABSTRACT

This invention concerns a process for obtaining proteoliposomes containing membrane proteins. This process is characterized by lipid vesicles being incubated in the reaction medium of an in vitro cell-free protein transcription/translation system.

7 Claims, 6 Drawing Sheets

Figure 1
A-
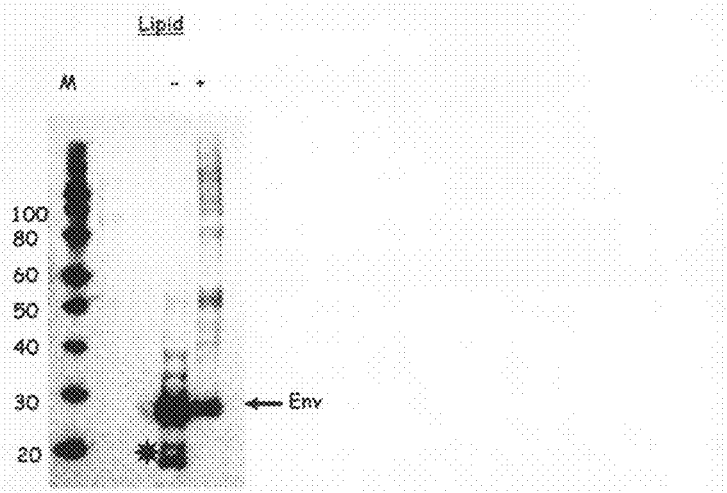
B-
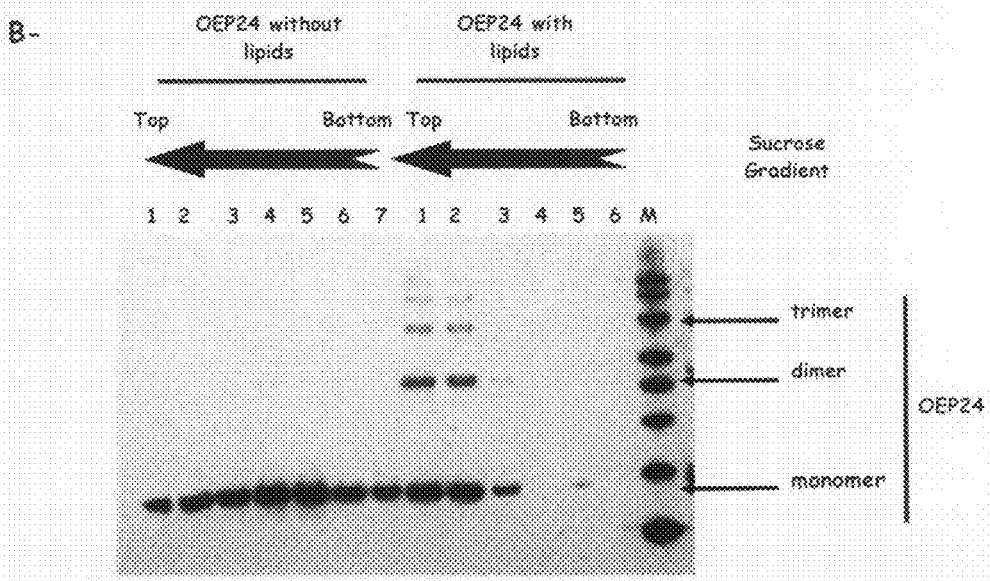

Figure 3
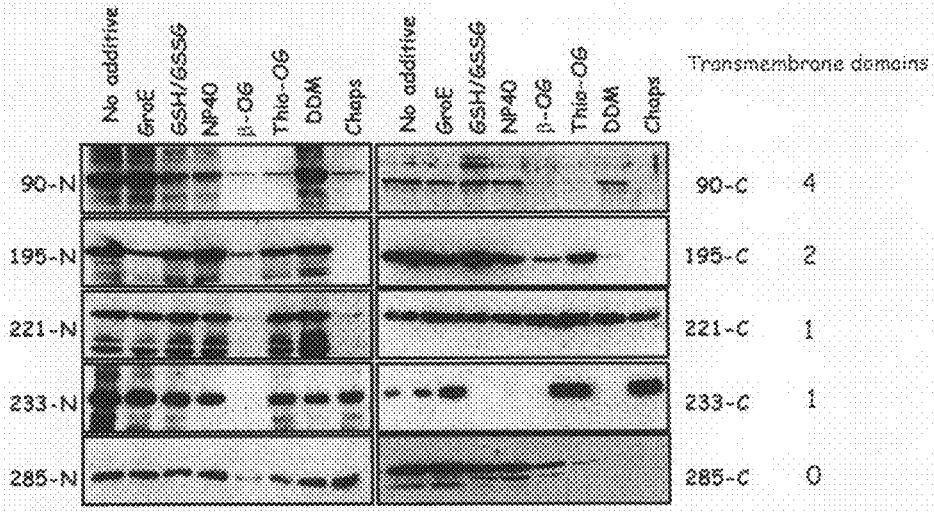
Figure 4
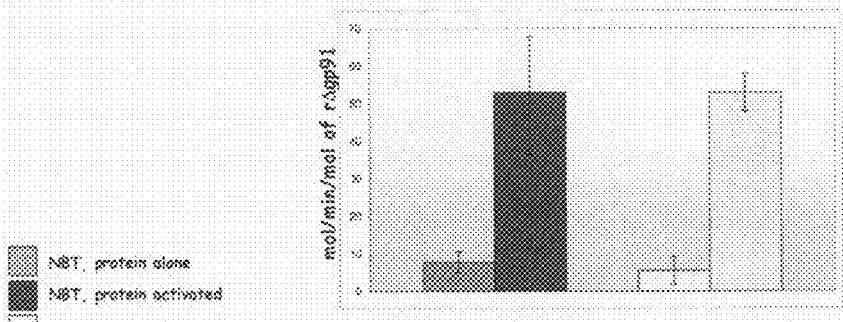
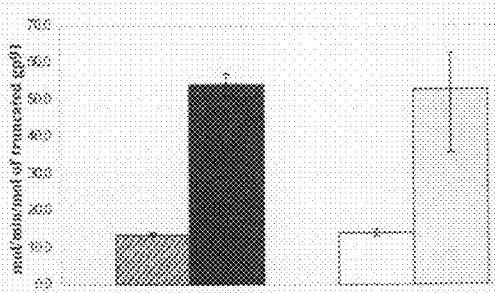

Figure 5
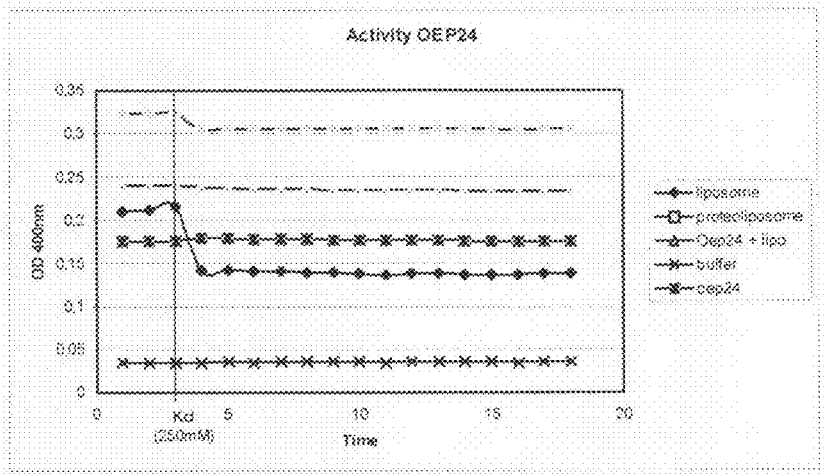
Figure 6
A- Cytochrome c
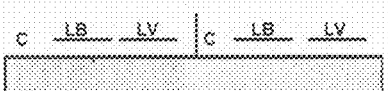
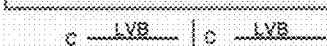
B- Caspase 9
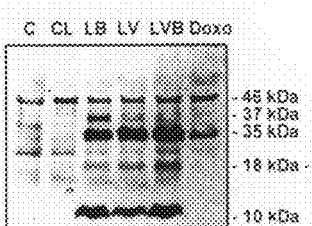
C- Caspase 7
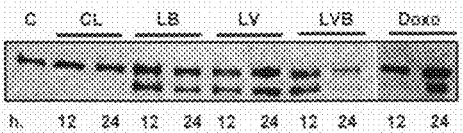
D- PARP
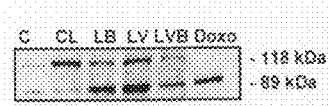

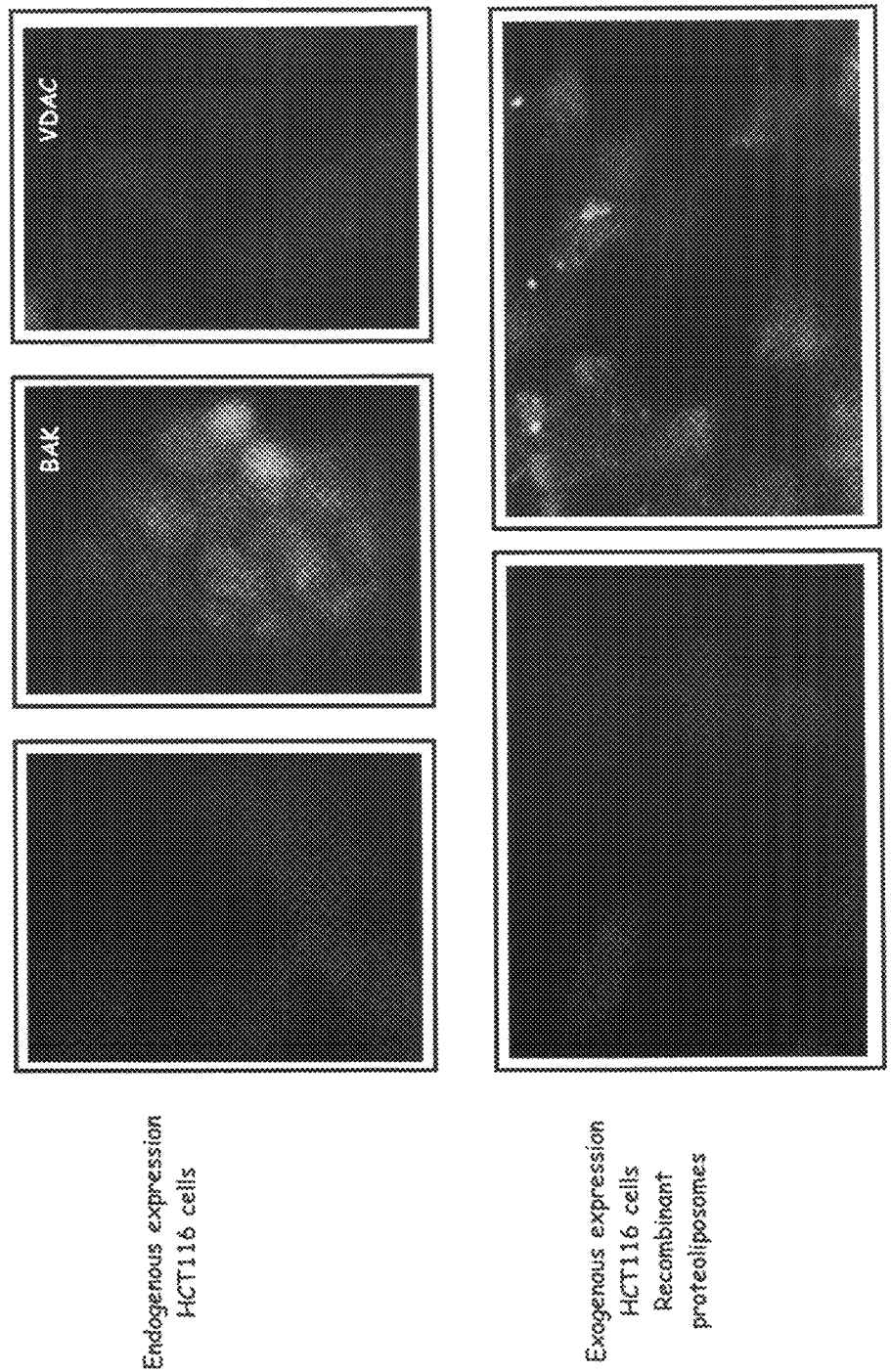

FORMATION OF PROTEOLIPOSOMES CONTAINING MEMBRANE PROTEINS BY MEANS OF AN ACELLULAR PROTEIN SYNTHESIS SYSTEM

TECHNICAL FIELD

This invention concerns novel and effective technology for producing membrane proteins integrated, in their native conformation and in an active form, into the lipid layer of liposomes.

The method according to the invention is based on use of the protein expression technique in an optimized cell-free translation system. In a single stage reaction, one or more recombinant membrane proteins of interest are integrated into a defined lipid bilayer, particularly of plant origin, to produce active proteoliposomes directly.

This process can be used on membrane proteins of various origins and with various structures and functions.

This technology is an effective and rapid tool for producing proteoliposomes for therapeutic or vaccine use.

PRIOR STATE OF THE ART

Recently there has been increasing interest in applying protein expression systems to biotechnology, based on the results of sequencing the genome of different species. Applications which can be envisaged, based on the expression of recombinant proteins, include the possibility of rapidly producing large quantities of soluble proteins for structural and functional studies, expressing vectorized therapeutic drug proteins, and the development of protein microplates for the study of protein/protein and protein/drug interactions.

Classic eukaryote or bacterial vector systems are widely used for recombinant protein production. While these systems represent powerful technologies, several of their aspects limit their usefulness. For example, with these systems it is difficult to obtain a reasonable quantity of functional membrane proteins for structural studies and it is even impossible to produce cytotoxic proteins.

Although these systems of protein overexpression are widely used, optimizing them seems to be essential. However this optimization appears difficult to achieve without modifying the cell functions of the living host organism.

A very interesting and attractive alternative for protein production is the use of cell-free transcription/translation systems (9, 12, 13, 14). These in vitro protein synthesis systems essentially use rabbit reticulocytes, lysates of the bacterium *Escherichia coli* or wheat germ.

One of the advantages of these in vitro systems is their ability to synthesize cytotoxic membrane proteins, regulator or unstable proteins, which cannot be expressed in living organisms, and therefore in classic in vivo systems. Moreover, another advantage of these cell-free systems is that they are completely open systems, in which each parameter of the reaction (such as pH, redox potential, ionic strength etc.) can be modified depending on the target protein to be produced. In addition in these systems, the resulting recombinant protein represents the major product of the reaction.

Currently, many research workers have opted for these synthesis systems as tools for structural and functional studies. Nevertheless, they are not at present a method of choice for large-scale protein production (5, 14).

A large number of recent studies have described methods to improve protein production in these cell-free systems. Studies have thus been reported using an improved *E. coli* lysate (3), on modified energetic mixtures (1), or on new reactant systems (4). Nevertheless, none of these studies has provided direct evidence of a subsequent increase in protein production.

Apart from their production, the transport of the proteins to their site of action is also very difficult.

Among the delivery systems available, liposomes have been identified as good candidates for delivery of macromolecules into cells, particularly for proteins in the form of proteoliposomes. Liposomes have the advantage of not being cytotoxic and can specifically carry and deliver a wide range of bioactive molecules (proteins, DNA, ribozymes etc.). They also protect the molecules from degradation and their composition is easily modifiable (10).

Various studies have already reported the use of liposomes for transporting soluble proteins such as antigens or toxins, drugs or nucleic acids. In the case of membrane proteins, the production of proteoliposomes requires at least a two-stage reaction, namely the production of the membrane protein then its integration into the liposome (8). In the case of proteins with a tendency to aggregate, an additional intermediate denaturation/renaturation step is necessary. Moreover, to the Applicant's knowledge no study has attempted to transport membrane proteins using liposomes.

As already stated, membrane proteins are proteins which are particularly difficult to over-produce in a non-aggregated active form. At the same time, membrane proteins represent about 30% of the total proteins of an organism and are involved in essential biological processes. Deregulation of their biological activity is one of the first responses of the cell to bacterial and viral infection, as well as occurring in cancers and genetic diseases.

However, methods for producing membrane proteins and functional proteoliposomes are particularly difficult to define, because of the intrinsic biochemical properties of these proteins. One of the major difficulties in studying membrane proteins is obtaining sufficient quantities of recombinant proteins using classic overexpression techniques.

Functional and structural studies of membrane proteins are therefore limited, on the one hand by this low production yield, and on the other, by these proteins mainly being obtained in an insoluble form due to their high hydrophobic amino acid content. To perform these studies, the membrane proteins must be denatured and renatured, and in certain cases integrated into liposomes. These stages are limiting and long and large quantities of the native form of membrane proteins cannot be obtained. As evidence of the difficulties encountered, the structure of only 120 membrane proteins has been determined to date.

There is therefore a continuing need for a reliable and simple system for producing membrane proteins in large quantities and in an active form.

DESCRIPTION OF THE INVENTION

In the first instance, the invention thus concerns a process for obtaining proteoliposomes containing membrane proteins. This process is characterized by the proteoliposomes being obtained by synthesizing the membrane proteins in vitro using a cell-free system in the presence of lipid vesicles which are added to the reaction medium.

The products obtained directly from this process are thus proteoliposomes containing membrane proteins in their native, active form.

"Containing membrane proteins" is taken to mean that the proteoliposomes contain at least one membrane protein. It is also possible to simultaneously produce and integrate several different types of recombinant membrane proteins in a single proteoliposome.

The membrane proteins, thus produced and packaged, may be of any origin: because of the numerous applications targeted, the membrane proteins integrated into proteoliposomes according to the invention are to advantage of mammalian or human origin. Where several membrane proteins (of different types) are contained in each proteoliposome, they can be of different origin.

The Applicant has likewise shown that this system also functions for membrane proteins with one or more transmembrane domains, thus irrespective of their structure and biochemical complexity.

In addition, it is possible to obtain functional membrane proteins irrespective of their function: channels, receptors, pro- or anti-apoptotic proteins, etc.

As previously stated, the process according to the invention allows the expression of proteins of various origins, such as eukaryote membrane proteins and more particularly those of mammals including one or more transmembrane domains (receptors, proapoptotic proteins, enzymes etc.), porins of bacterial origin but also from plants or mammals, or viral envelope proteins. Mutated or truncated forms of these proteins may also be expressed by this expression system and be integrated into lipid vesicles as long as they contain at least one hydrophobic domain.

The invention results from the Applicant choosing firstly to select an in vitro protein synthesis system and secondly to present the membrane proteins in the form of proteoliposomes, choices which were not obvious. Remarkably, the invention is carried out in a single stage, with very satisfactory quantitative and qualitative results.

A system of cell-free overexpression has therefore been developed and optimized for producing membrane proteins allowing both their synthesis to be improved in an active soluble form and their direct integration, in a single step, into liposomes to form proteoliposomes.

In practice, one or more recombinant membrane proteins are synthesized in vitro using a cell-free protein synthesis system (transcription/translation). These systems are well known to those skilled in the art and are available on the market, e.g. the RTS system (Rapid Translation System) 100HY or 500HY marketed by Roche Applied Science.

In such systems, the proteins of interest are synthesized from plasmids in which sequences are cloned encoding the said proteins or protein fragments.

In general, these sequences correspond to complementary DNA including an open reading phase encoding for a membrane protein containing either one or more transmembrane domains in an α helix, or forming a porin type β sheet, or containing a hydrophobic domain which combines with the lipid bilayer.

According to the invention, it is possible to synthesize proteoliposomes containing two distinct membrane proteins. In practice, each protein can be produced separately from a different plasmid. Alternatively and in a preferred way, the two sequences encoding the two proteins can be put into the same plasmid, and to advantage expressed from a single promoter.

A cell-free protein expression system which can be used for the invention is not limited to any particular source and can include wheat germ, *E. coli* lysates, rabbit reticulocytes, or *Xenopus laevis* oocytes. To advantage, the biological extract is an *E. coli* lysate.

According to the invention, lipid vesicles are added to the reaction medium, either during protein synthesis, or preferably even before the latter begins. This lipid addition is preferably made at a concentration of a few milligrams per ml of reaction medium, generally between 0.5 and 10 mg/ml.

Adding lipid agents to the reaction medium was already known, but a priori of the same type as the lysate used, i.e. generally lipids from *E. coli*, with the object of increasing the solubility of the neosynthesized proteins. On the other hand, to the Applicant's knowledge the addition of lipid vesicles with the aim of forming proteoliposomes has never been described or even suggested.

Lipid vesicles are lipid bilayers in the form of spheres with a diameter of approximately 100 nm, prepared using protocols known to those skilled in the art and known as SUV (Small Unilamellar Vesicles) (6, 15).

These lipid vesicles may be treated with a detergent before they are introduced into the reaction medium.

According to a first embodiment, the lipid vesicles used are of natural origin, preferably of plant origin, particularly from spinach.

In a preferred embodiment, the lipid vesicles are obtained from lipids from spinach chloroplasts. This is therefore a mixture of lipids, which are essentially anionic and derivatives of diacylglycerol (2). In the context of the invention, it has become clear that thylakoid liposomes are a choice universal material for the formation of proteoliposomes in a single step.

Alternately, the lipid vesicles may be liposomes of synthetic origin, i.e. produced from synthetic lipids.

According to a preferred embodiment and in particular in the case of synthetic lipids, the liposomes used in the invention bear molecules of polyethylene glycerol (PEG), or of derivatives of PEG (functionalized PEG) such as N-carbonyl-methoxy-polyethylene glycol 2000.

In practice, the PEG molecules or PEG derivatives may be grafted onto the lipids forming the lipid vesicles.

This embodiment is of particular interest in as far as it has been shown, in the context of this invention, that proteoliposomes obtained from this process are capable of transporting and releasing the membrane proteins of interest in vivo. The presence of PEG does not disturb the in vitro synthesis of membrane proteins at all, nor their integration and activity in the liposomes, while it increases their stability in vivo.

To advantage, the lipid vesicles used in the process according to the invention are not particles containing phospholipids and apolipoproteins (PAP).

To optimize the reaction, compounds chosen from the following list can be added, alone or in combination: detergents (cationic, anionic or zwitterionic), chaperones, redox couples, carbohydrate polymers, protease inhibitors, natural or synthetic lipids. The latter may first be treated with detergents or used directly in the reaction. The detergent DDM is particularly recommended because it favours the unidirectional insertion of membrane proteins in the lipid bilayer.

At the end of this process, the majority of the population of the reaction medium is made up of proteoliposomes. These proteoliposomes may be purified by any known technical means, and in particular on a discontinuous sucrose gradient. According to an estimation by silver staining, the fractions containing the recombinant proteoliposomes are a minimum of 90% pure at the end of this stage.

The proteoliposomes thus obtained contain the membrane proteins in their native conformation, without a denaturation and/or renaturation stage. This method makes it possible to obtain several hundred micrograms of pure functional membrane proteins per millilitre of initial reaction medium.

Another aspect of the invention therefore also concerns proteoliposomes containing membrane proteins in their native, functional conformation, integrated into the lipid bilayer. It should be noted that, through the process used in this invention, a very uniform population of proteoliposomes is obtained.

The nature of the lipid bilayer forming the proteoliposomes is directly linked to that of the lipid vesicles added to the reaction medium. To advantage the lipid bilayer is therefore of natural origin, more advantageously of plant origin. In a preferred embodiment, the proteoliposome contains lipids from spinach chloroplasts.

Alternatively, the proteoliposomes may contain synthetic lipids.

According to a preferred embodiment, the proteoliposomes according to the invention bear polyethylene glycerol (PEG) molecules, or PEG derivatives (functionalized PEG) such as N-carbonyl-methoxy-polyethylene glycol 2000.

The proteoliposomes according to the invention may be used for many applications:

They can be used directly as mini-cells.

They can be used to test the enzyme activity of integrated membrane proteins or for their structural analysis.

They can be used as vectors for the targeted release of membrane proteins to the plasma membrane or nuclear membrane, to the mitochondria or to certain organelles. These proteoliposomes can therefore be used as membrane protein transduction vectors (therapeutic membrane proteins as drugs, e.g. anti-tumour molecules), but also as vectors for the presentation of antigens containing native epitopes for the development of vaccines.

It is also possible to envisage destroying the proteoliposome in vitro, possibly by eliminating lipids to recover the membrane proteins as such, particularly for performing structural or functional studies.

Another aspect of the invention is that it provides a kit for obtaining proteoliposomes containing one or more membrane proteins of interest. Such a kit is composed of at least:

- a cell-free protein synthesis system, in which the gene or genes encoding the membrane proteins of interest is integrated;
- lipid vesicles as described above.

This description highlights the various advantages of this invention and the progress which results from it relative to the previous state of the art. Indeed, obtaining membrane proteins in sufficient quantity for functional and structural studies has represented a challenge for many years. None of the classic systems of overexpression provided an answer to this problem. On the contrary, the high hydrophobic amino acid content of membrane proteins resulted in the production of insoluble recombinant proteins, necessitating renaturing then integration into lipids in several stages to allow their behaviour to be studied.

EXAMPLES OF EMBODIMENTS

The invention and the advantages resulting from it are better illustrated by the following examples of embodiments and the attached figures. However, these examples are in no case exhaustive.

FIG. 1 represents the expression of the Env viral protein (A) and pea chloroplast porin OEP24 (B), in the presence or absence of lipid vesicles. The multimers of protein OEP24 are indicated by the arrows.

FIG. 3 shows the expression, in the presence or absence of different additives, of different truncated forms of the human gp91-phox protein containing an N (on the left) or a C terminal (on the right) histidine label.

FIG. 4 shows measurements of the activity of recombinant proteoliposomes containing a truncated form of gp91-phox in (A) one transmembrane domain and in (B) 4 transmembrane domains. The enzyme activity of recombinant proteoliposome diaphorases was measured in the presence of substrates such as INT or NBT and in the presence or absence of cytosol factors.

FIG. 5 shows the permeability to KCl of proteoliposomes containing OEP24 protein. The changes in turbidity of the proteoliposomes were measured at 400 nm in the presence of KCl.

FIG. 6 shows the proapoptotic activity of recombinant proteoliposomes containing VDAC protein (LV) or Bak protein (LB) or VDAC and Bak proteins (LVB). Lipid vesicles (L) alone acted as controls. The proapoptotic activity of the recombinant proteoliposomes was measured either in vitro by studying the release of cytochrome C from purified mitochondria after interaction with the proteoliposomes (A), or in vivo by measuring the cleavage of caspase 9 (B) and 7 (C) or of PARP protein (C) after interaction and internalization of the proteoliposomes in human colon carcinoma cells HCT116.

Figure 7:
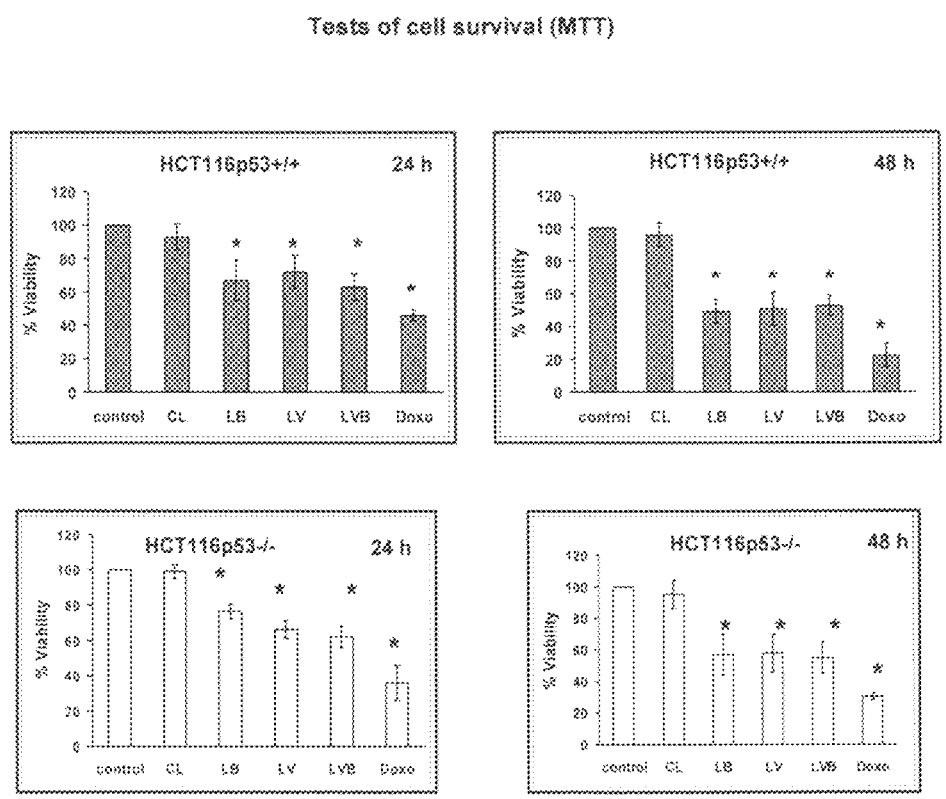

FIG. 7 shows the activity of recombinant proteoliposomes containing VDAC and/or Bak proteins (LV, LB and LVB) after internalization in human colon carcinoma cells containing the protein p53wt (HCT116p53+/+) or with a deletion of the p53 (HCT116p53−/−) gene. Cell survival was measured 24 hours or 48 hours after putting the proteoliposomes in contact with the cells. Liposomes alone (CL) and doxorubicin (Dx) were respectively used as negative and positive controls of the apoptosis induced.

FIG. 8 shows immunofluorescence images of the exogenous VDAC and Bak membrane proteins in human colon carcinoma cells (HCT116), after transduction and internalization of the proteoliposomes. The exogenous Bak and VDAC proteins were revealed using an anti-histidine antibody and the co-location of proteins with the mitochondria by staining with the Mitotracker. Endogenous VDAC and Bak proteins were revealed by specific antibodies directed against VDAC1 and Bak proteins.

MATERIAL AND METHODS

1—Construction of Expression Vectors:

A PCR product containing the complementary DNA encoding for the membrane protein of interest and including a promoter sequence, a T7 type terminator sequence, and an RBS (Ribosome Binding Site) located between 5 and 8 base pairs from the first methionine codon can be used as a matrix for the protein synthesis. Nevertheless, a prokaryote expression vector containing a promoter region, a T7 type terminator region and an RBS will generally be preferred. The vectors may, for example, be pET (Novagen) or pIVEX (Roche Applied Science).

In the case of co-expression of 2 membrane proteins, each of the complementary DNAs encoding respectively for these proteins is inserted in tandem including the second complementary DNA downstream of a second RBS sequence. Co-expression then occurs by a monocistronic method. For each of the membrane proteins of interest, a label is introduced in phase either on the N terminal side of the protein or on the C terminal side thus giving two constructs per complementary DNA. These labels can be of any origin (NusA, GST, MBP, etc.), and more particularly a label consisting of 6 or 8 histidine residues (6×-His or 8×-His). The position of these labels on the protein can have a major influence both on the expression of the protein and on its stability and solubility. Each of the constructs obtained is verified by a sequencing reaction, to check the integrity of the DNA sequence as well as fusion with the labels.

The complementary DNAs of VDAC, Bak, OEP24 and gp91-phox are amplified by the PCR technique using forward and reverse primer couples which allow direct integration in phase with cutting by appropriate restriction enzymes, in the expression vectors pIVEX2.3MCS, pIVEX2.4NdeI (Roche Applied Science) and/or pet15b, pet30b (Novagen). Constructs encoding for the truncated forms of gp91-phox use the same cloning strategy integrating the restriction sites in the primers as described below:

Forward Primers:
5'GGAATTCCATATGGTTCGAAGACAACTG-GACAGG3' for gp91$^{phox}$ 90 (SEQ ID 1), 5'GGAATTC-CATATGAAAACCATCCGGAGGTCTTAC3' for gp91$^{phox}$ 195 (SEQ ID 2), 5'GGAATTCCATATGATCCATGGAGCT-GAACGAA3' for gp91$^{phox}$ 221 (SEQ ID 3), 5'GGAATTC-CATATGGCAGAGAGTTTGGCTGTG3' for gp91$^{phox}$ 233 (SEQ ID 4) and 5'GGAATTCCATATGTTTTGGCGATCT-CAACAGA3' for gp91$^{phox}$ 285 (SEQ ID 5) containing an NdeI site on the 5' side.

Reverse Primers:
5'GCGTTACTCGAGTCATGGAAGAGA-CAAGTTAGAAG3' (SEQ ID 6) for the label in the N-terminal position or
5'GCGTTACTCGAGGAAGTTTTCCTTGT-TGAAAATG3' (SEQ ID 7) for the label situated on the C-terminal side. These primers contain an XhoI restriction site.

2—Preparation of the Lipid Vesicles

A—Preparation of the Intact Chloroplasts

The chloroplasts are prepared following the method described by Douce and Joyard (1982), with a few modifications. The chloroplasts are extracted from the leaves of spinach (*Spinacia oleracea* L.). The leaves are sorted, their ribs removed, then they are washed. The leaves thus obtained are kept for one night in a cold room to exhaust the starch reserves present in the plasts. The leaves (about 2 kg for 2 l of blending medium: sucrose 0.33 M, sodium pyrophosphate 30 mM, BSA 1 g/l, pH 7.8) are finely chopped in a blender (type Waring Blendor, 4 l volume) for 2 to 3 seconds at 4° C. The homogenate is filtered on 4 thicknesses of gauze and a 50 µm mesh blotting cloth. The filtrate is centrifuged at 1200 g for 10 min at 4° C. The pellets are gently diluted with washing medium (sucrose 0.33 M, MOPS/NaOH 20 mM, pH 7.8). This chloroplast rich suspension is filtered on a 50 µm mesh blotting cloth. To eliminate extrachloroplastic contaminants and broken chloroplasts, the suspension is placed on a discontinuous gradient of Percoll (Percoll 40% [(v/v)], sucrose 0.33 M, MOPS/NaOH 20 mM, pH 7.8 and Percoll 80% [(v/v)] sucrose 0.33 M, MOPS/NaOH 20 mM, pH 7.8) and centrifuged at 3000 g for 20 min. The intact chloroplasts are localized at the interface between the layers of Percoll 40 and 80% [(v/v)], while non-chloroplastic material and broken chloroplasts remain above the Percoll 40% [v/v] layer. To eliminate the Percoll, the intact chloroplasts are diluted with 6 to 7 volumes of washing medium and centrifuged at 4000 g for 5 min. The pellet is recovered in washing buffer, filtered on 50 µm mesh blotting cloth then centrifuged at 3000 g for 5 min.

B—Purification of the Thylakoids

The thylakoids are purified following the protocol described by Douce et al. (2) with a few modifications. The intact chloroplasts are put into a hypotonic medium (MgCl$_2$ 4 mM, MOPS/NaOH 10 mM, pH 7.8). The volume of the hypotonic medium is approximately 10 times greater than that of the chloroplasts. The final sucrose concentration is thus severely reduced to less than 0.1 M. The suspension of broken chloroplasts is put onto a discontinuous sucrose gradient (sucrose 0.6 M and 0.93 M in MgCl$_2$ buffer 4 mm, MOPS/NaOH 10 mM, pH 7.8) and centrifuged at 72000 g for 1 hr. After centrifuging, three fractions are obtained: an upper layer of the gradient which contains the chloroplast's soluble enzymes (the stroma), a green pellet which essentially contains thylakoids, and the chloroplast envelope localized at the interface of the 0.6 M and 0.93 M sucrose layers.

C—Purification of the Lipids by Chromatography on a Silica Column

As the lipid composition of the chloroplast and thylakoid envelopes is similar, the latter have been used as they are obtained in greater quantity. The total lipids are extracted according to the method described by Bligh & Dyer (1959), with a few modifications. The thylakoids are solubilized in washing buffer or distilled water, then the suspension is centrifuged at 1000 g at 4° C. for 10 min. The pellet is solubilized in CHCl$_3$/MeOH (1/2) to which a third of the volume of CHCl$_3$ and a third of distilled water is added. The solution is kept at 4° C. overnight. The organic phase (dark green, containing the lipids and pigments) is recovered then evaporated to dryness under argon and solubilized in pure CHCl$_3$. This solution is placed on a silica gel column as described by Dome et al. (1987) to eliminate the pigments. The column is washed in advance using a volume of CHCl$_3$ and stoppered with quartz wool. The silica (<325 mesh) is dissolved in pure CHCl$_3$. When the CHCl$_3$ reaches the top of the gel the solution is deposited. A column volume of CHCl$_3$ is added (to eliminate the pigments) until a translucent eluate is obtained. All the CHCl$_3$ is then eluted and a mixture of CHCl$_3$/acetone (990/10) is used to elute the monogalactosyldiacylglycerol (MGDG). The eluate is recovered, evaporated to dryness under argon and solubilized in a mixture of CHCl$_3$/MeOH (1/2). Methanol is then added (elution of the digalactosyldiacylglycerol (DGDG), sulfoquinovosyldiacylglycerol (SQDG), and trigalactosyldiacylglycerol (TGDG)). The eluate is recovered, evaporated to dryness under argon and solubilized in a mixture of CHCl$_3$/MeOH (1/2). The sample is evaporated again and redissolved in 3 ml of CHCl$_3$/MeOH (1/2) and kept under argon at −20° C.

D—Formation and Purification of the Lipid Vesicles

The lipids are evaporated under argon and resuspended in DEPC (diethylpyocarbonate) treated or nuclease-free water. The lipids are sonified (Branson Sonifer 250, cycle 0.5 and amplitude 80) 3×1 min to form a homogeneous suspension containing SUVs (Small Unilamellar Vesicle). The suspension is filtered on a 0.2 µm membrane to obtain a suspension of lipid vesicles (liposomes) of uniform size.

3—Expression of the Membrane Proteins

The membrane proteins are synthesized in a cell-free expression system. This system is based on an *Echerichia coli* lysate as described by Spirin (11) or Liguori (7). The reactions are carried out either in batch format (in Eppendorff tubes or multiwell plates), or in cups (RTS500HY system from Roche Applied Science).

The components of the reaction are as follows:

*E. coli* lysate (RTS system [Roche Applied Science], RiNA system [Quiagen] or Expressway system [Invitrogen])

The energetic medium

All the amino acids except methionine

Methionine

Non-ionic or zwitterionic detergents

GroE or DnaK chaperones

Carbohydrate polymers (NV10 [Novexin])

Protease inhibitors (e.g. Protease Inhibitor Tablet [Roche Applied Science])

They are mixed in the presence of the plasmid DNA or the PCR product encoding for the membrane protein. The reactions are incubated while being stirred (180 rpm to 990 rpm) in a water bath or Proteomaster (Roche Applied Science) for 12 to 48 hours at 20° C. In the case of single stage formation of proteoliposomes, once the reaction mixture has been made, the thylakoid lipid vesicles are added volume for volume to the reaction mixture at a concentration varying between 0.6 mg/ml to 10 mg/ml. The reaction medium/lipid vesicle mixture is then gently homogenized. In the event of co-expression of 2 membrane proteins, the 2 expression vectors (in equimolar quantities) or the co-expression vector in the monocistronic method depending on a T7 promoter, are added to the reaction volume and incubated as described above in the presence or absence of liposomes. The reactions are incubated as described earlier.

4—Purification of the Proteoliposomes

The proteoliposomes produced during cell-free synthesis in a batch or cups are purified on a discontinuous sucrose gradient. The reaction mixture is first centrifuged at 13,000 rpm for 20 min at 4° C., then the supernatant is removed and the pellet containing the proteoliposomes (green pellet) is resuspended in a volume equivalent to the reaction volume with Tris-HCl 50 mM, pH 7.2. The resuspended samples are deposited between the 60% sucrose (1 to 6 ml of sucrose) and the 25% sucrose (1 to 6 ml of sucrose) layers. The whole system is then carefully covered by a layer of 10% sucrose (0.4 to 2 ml of sucrose). After centrifuging for 1 hour at 200,000 g at 4° C., 0.1 to 1 ml fractions are collected from the top of the gradient and are analyzed by western blotting, silver and/or Coomassie blue staining to determine the final protein concentration and the purity of the membrane proteins integrated into the liposome. The activity of the membrane proteins contained in each fraction is tested either by enzyme reaction (in the case of truncated forms of gp91-phox), or by analyzing the function of the proteins after transduction into mammalian cells (in the case of Bak and VDAC proteins). Fractions containing a high degree of purity of proteoliposomes are grouped and tested in transduction experiments in mammalian cells.

5—Cell Transduction of Membrane Proteins Contained in the Proteoliposomes

The purified proteoliposomes are tested for their capacity to transduce the recombinant membrane proteins into mammalian cells. The purified proteoliposomes are directly added at a concentration of 0.6 μM to 1.5 μM to $1\times10^6$ cells and are incubated at 37° C., 5% CO2, for 6, 12 or 24 hours before analysis. The cellular location of the exogenous recombinant membrane proteins is detected by immunofluorescence using membrane protein specific antibodies or an anti-histidine antibody. The activities of the recombinant membrane proteins, particularly Bak and VDAC are tested by determining cell viability (MTT, Annexin V tests etc.), by activating proteins involved in apoptosis (caspase 3, 7, 9, 8, PARP, p53 etc.) after incubation.

Results

1—Expression of Membrane Proteins in the Presence of Thylakoid Lipids

Figure 2:
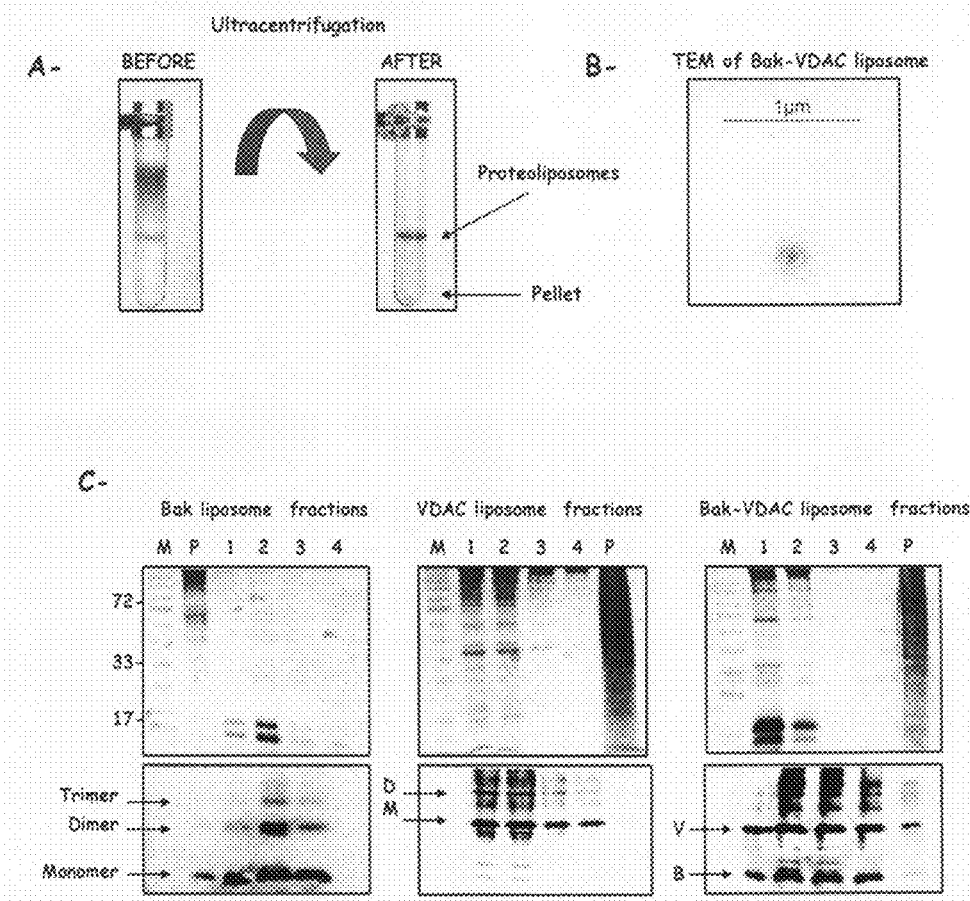
FIG. 2 illustrates the analysis of recombinant proteoliposomes. (A) Purification of the proteoliposomes on a sucrose gradient. (B) Electron microscope analysis of purified recombinant proteoliposomes. (C) SDS-PAGE gel analysis and silver nitrate staining of the different fractions of the sucrose gradients.

In order to determine the influence of thylakoid lipids on the synthesis of membrane proteins, in vitro expression reactions are carried out in the presence or absence of thylakoid lipid vesicles (FIGS. 1A and 1B). Batch reactions in a final volume of 25 μl, 50 μl or 100 μl are performed in the presence of lipid vesicles (liposomes) at an initial concentration of 10 mg/ml. The volume of liposomes added is at least equal to that of the synthesis reaction volume (vol/vol). The final concentration of liposomes in the synthesis reaction can vary from 0.6 mg/ml to 5 mg/ml. The liposomes are added to the reaction medium once the reaction mixture has been made. Interestingly, the presence of lipids does not interfere with the transcription and translation machinery of the in vitro expression system (FIG. 1). The in vitro expression system based on an *E. coli* lysate can synthesize proteins of various origins such as viral envelope proteins (Env protein, FIG. 1A), plant proteins (porin OEP24, FIG. 1B), bacterial (results not shown) or mammalian (porin VDAC and mitochondrial proapoptotic protein BAK, FIG. 2C) membrane proteins. Moreover, the addition of lipid vesicles has a positive effect on the synthesis of certain membrane proteins and on their structure, since, for example, they provide protection against the breakdown of neosynthesized membrane proteins (Env protein, FIG. 1A), they allow the formation of multimers (porin OEP24, FIG. 1B and mitochondrial proteins VDAC and BAK, FIG. 2C), the co-expression of membrane proteins (FIG. 2C), or conservation of protein function (mitochondrial proteins VDAC and BAK, FIGS. 6 and 7, and gp91-phox, FIG. 4) which they do even in the absence of additives such as chaperones and detergents.

2—Production of membrane proteins in the presence of liposomes and additives

Due to the structural complexity of certain membrane proteins, the synthesis in soluble and active form of membrane proteins including several transmembrane domains (such as α helix domains) requires the addition of chemical compounds which allow their native conformation to be maintained and their uni- or bi-directional integration into the lipid bilayer of the liposomes. Various studies on membrane proteins have demonstrated that the use of ionic, non-ionic or zwitterionic detergents is necessary to extract and/or resolubilize membrane proteins. These detergents are then eliminated during the last stages of proteoliposome formation by dialysis, by exclusion chromatography, by dilution or by the addition of polystyrene beads.

The effect of non-ionic (n-dodecyl β-D-maltoside [DDM], n-octyl β-D-glucopyranoside [β-OG], n-thiooctyl β-D-glucopyranoside [β-thioOG], nonylphenyl-polyethylene-glycol [NP40], polyoxyethylene-(23)-lauryl-ether [Brij-35], polyoxyethylene-(8)-lauryl-ether [C12E8], polyoxyethylene-sorbitan-monolaurate 20 [Tween 20], n-decyl-β-D-maltoside [DM]) and zwitterionic (3-[(3-cholamidopropyl)dimethylammonio]-1-propanesulphonate [CHAPS], Zwittergent 3-14, lauryldimethylamine oxide [LDAO]) detergents has been tested on the expression, solubility and integration of membrane proteins in thylakoid liposomes. Several series of experiments have thus been performed on different truncated forms of the human protein gp91-phox in the presence of detergents only and/or in the presence of chaperones (DNAK, GroE), a redox couple (GSH/GSSG), a carbohydrate polymer (NV10, Novexin) and protease inhibitors (FIG. 3). All the detergents are added to the reaction medium at a concentration greater than their critical micellar concentration (CMC) except n-dodecyl β-D-maltoside [DDM] which is used at a concentration close to the CMC (0.2 mM for a theoretical CMC of 0.12 mM). As shown in FIG. 3, these detergents have varying effects on the expression of the membrane proteins. For example, CHAPS and β-OG have a negative effect on the expression of truncated forms of gp91-phox except for constructs gp91$^{phox}$ 221-C for β-OG and gp91$^{phox}$ 221-C, gp91$^{phox}$ 233-N and 233-C, gp91$^{phox}$ 285-N for CHAPS. In contrast, the detergents NP40, Thio-OG and DDM stimulate the expression of most truncated forms of gp91-phox with a greater effect for constructs containing a hexa-histidine label at the N-terminal end of the protein (FIG. 3). These results suggest that the addition of non-ionic detergents is compatible with the synthesis of membrane proteins with one or more α helix transmembrane domains and that they can be added in the synthesis reaction for proteoliposome formation.

Experiments synthesizing membrane proteins with one or more a helix transmembrane domains were carried out in the presence of detergents and liposomes for the formation of proteoliposomes. The preceding results have demonstrated that the detergent DDM at a concentration close to its CMC stimulated the expression and solubility of different truncated forms of the gp91-phox protein in the majority of cases. The detergent DDM was therefore selected for preference in the proteoliposome formation experiments. It has also been shown that because of its biochemical properties, DDM favours the unidirectional integration of membrane proteins into lipid bi-layers. Truncated forms of the gp91-phox protein containing one or more protein transmembrane domains have been produced in the presence of DDM and lipid vesicles. The proteoliposomes were then purified on a sucrose gradient and the diaphorase activity of the fractions containing the purified proteoliposomes was tested in the presence of NBT or INT.

3—Functional Activity of Proteoliposomes Synthesized in an in vitro System

The enzyme activity of proteoliposomes containing the different truncated forms of gp91-phox was determined in the presence of 2 substrates as electron acceptors: NitroBlueTetrazolium (NBT) and IodoNitroTetrazolium (INT). Unlike soluble truncated gp91-phox proteins, proteoliposomes have an NADPH and FAD dependant enzyme activity without the addition of cytosol factors and arachidonic acid (FIG. 4). For example, the diaphorase activity of the proteoliposome containing the gp91-phox 221C protein in the presence of the 2 cofactors has a basal activity of 7.8 mol/min/mol for the reduction of NBT and 5.5 mol/min/mol for INT (FIGS. 4A and 4B). These values are close to those of the soluble protein and indicate that the proteoliposome is fully functional. Incubation of 10 nmoles of recombinant proteoliposomes containing gp91 phox-221C with cytosol extracts and arachidonic acid increases the reductase activity of the protein by a factor of 7 for NBT and 10 for INT (FIGS. 4A and 4B). These results thus indicate that the recombinant membrane proteins contained in the lipid vesicles have basal enzyme activities which can be stimulated by the addition of cytosol factors and arachidonic acid.

In order to determine the activity of proteoliposomes containing porin OEP24, activity tests were undertaken by measuring differences in absorption at 400 nm (FIG. 5). Lipid vesicles containing or not containing OEP24 were first equilibrated in a solution containing 10 mM of Tris-Hepes, pH 7.0 and 10 mM of KCl. The absorbance at 400 nm was measured for 15 sec then osmoticum (KCl 250 mM final) was added to the medium. The variations in absorbance were measured periodically over 2 minutes. In the presence of KCl, the empty lipid vesicles (without OEP24) showed a change in absorption at 400 nm due to osmotic shock. The proteoliposomes containing the membrane protein OEP24 showed no change in absorption at 400 nm indicating that the lipid vesicles are permeable to the osmoticum added (FIG. 5). These results demonstrate that the OEP24 protein is fully active and is for the most part integrated in the sense orientation in the lipid bilayer.

The proteoliposomes containing the pro-apoptotic Bak and/or VDAC proteins were put into the presence of purified mitochondria to measure the release of cytochrome c. As shown in FIG. 6A, the proteoliposomes containing VDAC and/or Bak proteins induce massive release of cytochrome c into the supernatant compared with control liposomes. These results indicate that the recombinant proteoliposomes interact directly with the external membrane of the mitochondria and induce cytochrome c release. All these results confirm that single stage synthesis rapidly produces fully functional proteoliposome preparations containing membrane proteins of varying complexity in the positive orientation.

4—Examples of Therapeutic Applications of Proteoliposomes Formed in vitro

An example of an application is shown in FIGS. 6B, 6C, 6D, 7 and 8. In order to measure the in vivo proapoptotic activity of VDAC and Bak proteins inserted in the lipid vesicles, human colon carcinoma cells (HCT116) are incubated in the presence of recombinant proteoliposomes for 24 and 48 hours. The location of exogenous membrane proteins is confirmed by immunofluorescence (FIG. 8B) and the proapoptotic activity is measured either by stimulating the caspase pathway (FIGS. 6B, 6C and 6D), or by measuring cell viability (FIG. 7). These results indicate that the recombinant proteoliposomes are capable of specifically releasing the membrane proteins of therapeutic interest to the external membrane of mitochondria and of inducing apoptosis in the target cells. In an identical way, the proteoliposomes are capable of releasing the truncated form of gp91-phox to the plasma membrane (results not shown).

To conclude, the single stage formation of recombinant proteoliposomes involving one or more membrane proteins may represent a method of choice for the development of vectors for the release of membrane proteins for therapeutic or antigenic purposes, for screening chemical drugs which interact with membrane proteins, for studying structural and functional membrane proteins and for setting up kits for the rapid synthesis of membrane proteins.

REFERENCES (1) Calhoun K A, Swartz J R. (2005) Energizing cell-free protein synthesis with glucose metabolism. *Biotechnol Bioeng,* 90(5), 606-613.

(2) Douce R, Holtz R B, Benson A A. (1973) Isolation and properties of the envelope of spinach chloroplasts. *J Biol Chem.* 248(20):7215-22.

(3) Kim D M, Swartz J R. (2000) Prolonging cell-free protein synthesis by selective reagent additions. *Biotechnol Prog,* 16(3), 385-390.

(4) Kim T W, Kim D M, Choi C Y. (2006) Rapid production of milligram quantities of proteins in a batch cell-free protein synthesis system. *J Biotechnol,* 124(2):373-80.

(5) Lamla T., Mammeri K. and Erdmann V A (2001) The cell-free protein biosynthesis: applications and analysis of the system. *Acta Biochim Pol.* 48(2):453-65.

(6) Lasic D D (1997) in Liposomes in gene delivery. CRC Press LLC (7) Liguori L, Marques B, Villegas-Mendez A, Rothe R and J L Lenormand (2007), Production of membrane proteins using cell-expression systems. *Expert Rev Proteomics.* 4(1): 79-90.

(8) Rigaud J L, (2002) Membrane proteins: functional and structural studies using reconstituted proteoliposomes and 2-D crystals. *Braz. J. Med. Biol. Res.* 35(7):753-766.

(9) Ryabova L A, Morozov Iyu and Spirin A S (1998) Continuous-flow cell-free translation, transcription-translation, and replication-translation systems. *Methods Mol Biol.* 77:179-93.

(10) Service R F, (2005) Nanotechnology takes aim at cancer. *Science* 310(5751), 1132-1134.

(11) Spirin A S (2002): in Cell-free translations systems. *Springer*, 3-20.

(12) Spirin A S (2004) High-throughput cell-free systems for synthesis of functionally active proteins. *Trends Biotechnol* 22: 538-545

(13) Swartz J R (2003) *Cell-Free Protein Expression:* A Springer press, Springer Berlin, Heidelberg, N.Y.

(14) Swartz J R (2006) Developing cell-free biology for industrial applications. *J Ind Microbiol Biotechnol.* 33(7): 476-85.

(15) Templeton N S, Lasic D D, Frederick P M, Strey H H, Roberts D D and Pavlakis G N (1997) Improved DNA:liposome complexes for increased systemic delivery and gene expression. Nature Biotech. 15(7): 647-652.

---

The invention claimed is:

1. A single-step process for producing proteoliposomes containing membrane proteins, the process consisting essentially of expressing membrane proteins in an in vitro cell-free expression system that includes lipid vesicles containing a lipid bilayer, wherein the lipid vesicles are present in the in vitro cell-free expression system at a concentration of 0.5 mg/ml to 10 mg/ml, thereby producing proteoliposomes containing a lipid bilayer and active membrane proteins integrated into the lipid bilayer in their native, functional conformation.

2. The single-step process according to claim 1, wherein the lipid vesicles contain polyethylene glycol (PEG) molecules or derivatives thereof.

3. The single-step process according to claim 2, wherein the polyethylene glycol (PEG) molecules or derivatives thereof are attached to synthetic lipids of the lipid vesicles.

4. The single-step process according to claim 1, wherein the lipid vesicles contain lipids of plant origin.

5. The single-step process according to claim 4, wherein the lipids of plant origin are obtained from spinach chloroplasts.

6. The single-step process of claim 1, wherein the in vitro cell-free expression system is free of detergent.

7. A single-step process for producing proteoliposomes containing membrane proteins, the process consisting essentially of expressing membrane proteins in an in vitro cell-free expression system that includes lipid vesicles containing a lipid bilayer, wherein the lipid vesicles are present in the in vitro cell-free expression system at a concentration of 0.5 mg/ml to 10 mg/ml, thereby producing proteoliposomes containing a lipid bilayer and active membrane proteins, wherein the process is performed free of detergent.

* * * * *

SEQUENCE LISTING

<160> NUMBER OF SEQ ID NOS: 7

<210> SEQ ID NO 1
<211> LENGTH: 34
<212> TYPE: DNA
<213> ORGANISM: Artificial sequence
<220> FEATURE:
<223> OTHER INFORMATION: Synthetic oligonucleotide; gp91phox 90

<400> SEQUENCE: 1
ggaattccat atggttcgaa gacaactgga cagg                34

<210> SEQ ID NO 2
<211> LENGTH: 34
<212> TYPE: DNA
<213> ORGANISM: Artificial sequence
<220> FEATURE:
<223> OTHER INFORMATION: Synthetic oligonucleotide; gp91phox 195

<400> SEQUENCE: 2
ggaattccat atgaaaacca tccggaggtc ttac                34

<210> SEQ ID NO 3
<211> LENGTH: 32
<212> TYPE: DNA
<213> ORGANISM: Artificial sequence
<220> FEATURE:
<223> OTHER INFORMATION: Synthetic oligonucleotide; gp91phox 221

<400> SEQUENCE: 3
ggaattccat atgatccatg gagctgaacg aa                  32

<210> SEQ ID NO 4
<211> LENGTH: 31
<212> TYPE: DNA
<213> ORGANISM: Artificial sequence
<220> FEATURE:
<223> OTHER INFORMATION: Synthetic oligonucleotide; gp91phox 233

<400> SEQUENCE: 4
ggaattccat atggcagaga gtttggctgt g                   31

<210> SEQ ID NO 5
<211> LENGTH: 32
<212> TYPE: DNA
<213> ORGANISM: Artificial sequence
<220> FEATURE:
<223> OTHER INFORMATION: Synthetic oligonucleotide; gp91phox 285

<400> SEQUENCE: 5
ggaattccat atgttttggc gatctcaaca ga                  32

```
<210> SEQ ID NO 6
<211> LENGTH: 35
<212> TYPE: DNA
<213> ORGANISM: Artificial sequence
<220> FEATURE:
<223> OTHER INFORMATION: Synthetic oligonucleotide; primer reverse Nterm

<400> SEQUENCE: 6
gcgttactcg agtcatggaa gagacaagtt agaag                              35

<210> SEQ ID NO 7
<211> LENGTH: 34
<212> TYPE: DNA
<213> ORGANISM: Artificial sequence
<220> FEATURE:
<223> OTHER INFORMATION: Synthetic oligonucleotide; primer reverse Cterm

<400> SEQUENCE: 7
gcgttactcg aggaagtttt ccttgttgaa aatg                               34
```